United States Patent [19]

Hardt et al.

[11] Patent Number: 5,087,745
[45] Date of Patent: Feb. 11, 1992

[54] PROCESS FOR THE PRODUCTION OF GAMMA-BUTYROBETAINE

[75] Inventors: Peter Hardt, Visp; Andrej Stravs, Ried bei Brig; Pius Abgottspon, Stalden, all of Switzerland

[73] Assignee: Lonza Ltd., Gampel/Valais, Switzerland

[21] Appl. No.: 667,367

[22] Filed: Mar. 12, 1991

Related U.S. Application Data

[63] Continuation of Ser. No. 409,792, Sep. 20, 1989, abandoned.

[30] Foreign Application Priority Data

Sep. 21, 1988 [CH] Switzerland ............ 3514/88

[51] Int. Cl.$^5$ ............ C07C 227/18; C07C 229/06
[52] U.S. Cl. ............ 562/553; 570/172
[58] Field of Search ............ 562/553; 560/172

[56] References Cited

U.S. PATENT DOCUMENTS

| | | | |
|---|---|---|---|
| 2,313,573 | 3/1943 | Orthner et al. | 560/172 |
| 2,367,878 | 1/1945 | Lee | 560/172 |
| 3,466,364 | 9/1969 | Takahashi et al. | 560/172 |
| 3,711,549 | 1/1973 | Phillips et al. | 260/563 |
| 3,796,632 | 3/1974 | Fukumura | 195/29 |
| 4,371,618 | 2/1983 | Cavazza | 435/128 |
| 4,567,140 | 1/1986 | Voelskow et al. | 435/42 |
| 4,650,759 | 3/1987 | Yokozeki et al. | 435/128 |
| 4,708,936 | 11/1987 | Kulla et al. | 435/128 |
| 4,806,282 | 2/1989 | Tinti et al. | 562/553 |

FOREIGN PATENT DOCUMENTS

| | | |
|---|---|---|
| 0122794 | 10/1984 | European Pat. Off. |
| 1903076 | 8/1969 | Fed. Rep. of Germany |
| 1939759 | 3/1970 | Fed. Rep. of Germany |
| 2751134 | 5/1979 | Fed. Rep. of Germany |
| 1198414 | 7/1970 | United Kingdom |

OTHER PUBLICATIONS

Aksnes et al., J. Chem. Soc., (1959), pp. 103ff.
Lindstedt et al., Biochemistry, vol. 16, No. 10, pp. 2181-2188, (1977).
Lindstedt et al., Biochemistry, vol. 6, No. 5, pp. 1262-1270, (1967).
J. H. Miller, Experiments in Molecular Genetics, Cold Spring Laboratory, pp. 121 to 143, Experiments 13-17.
P. Gerhardt et al., "Manual of Methods for General Bacteriology", Am. Soc. Microbio., pp. 222-242, (1981).
J. P. Vandecasteele, Appl. Environ. Microbio., vol. 39, No. 2, pp. 327-334, (1980).
Kulla et al., Arch. Microbiology, vol. 135, pp. 1-7, (1983).
Perry's Chemical Engineer's Handbook, 6th Ed., p. 27-7, (1989).
L. N. Ornston et al., Biochem. and Biophys. Res. Comm., vol. 36, No. 1, pp. 179-184, (1969).
Seim et al., European Congress of Biotechnology, 3rd Ed., vol. 1, pp. 481-486, (1984).

Primary Examiner—J. E. Evans
Attorney, Agent, or Firm—Fisher, Christen & Sabol

[57] ABSTRACT

Process, which is feasible on a commercial scale, for the production of gamma-butyrobetaine. For this purpose, butyrolactone with hydrogen chloride and an alcohol is converted to the chlorobutyric acid ester, the trimethylammonium butyric acid salt is formed with trimethylamine and then saponified to the end product.

4 Claims, No Drawings

PROCESS FOR THE PRODUCTION OF GAMMA-BUTYROBETAINE

This application is a continuation of prior U.S. application Ser. No. 409,792, filing date Sept. 20, 1989, now abandoned.

BACKGROUND OF THE INVENTION

1. Field Of The Invention

The invention relates to a process for the production of gamma-butyrobetaine.

2. Background Art

Gamma-butyrobetaine is finding increasing use as an initial product for the microbiological production of L-carnitine. Laboratory processes for the synthesis of the individual intermediate steps have been sufficiently described.

According to West German OS 2,751,134, gamma-butyrolactone can be reacted with thionyl chloride and methanol in a 91 percent yield into l-chlorobutyric acid methyl ester. The necessary disposal of the resultant $SO_2$ is a drawback in this process.

It can be seen from West German OS 1,903,076 that gamma-butyrolactone can be converted into the gamma-chlorobutyric acid methyl ester with dry hydrochloric acid and methanol with 4-hour refluxing and after one-week standing of the reaction solution.

It can be gathered from West Germany OS 1,939,759 that gamma-butyrolactone can be converted into the gamma-chlorobutyric acid methyl ester in a two-step process (first step with zinc chloride and hydrochloric acid; second step with methanol under reflux conditions) with a yield of 90 to 95 percent. But a great disadvantage is the amount of zinc salt formed that cannot be recycled and heavily loads the waste water.

From Aksnes et al., J. Chem. Soc., (1959), p. 103 ff, it is further known that gamma-bromobutyric acid methyl ester can be converted into the 4-trimethylammonium butyric acid methyl ester by heating with alcoholic trimethylamine in a yield of only 20 percent.

The above-mentioned process steps, thus, produce either highly unsatisfactory yields or, because of the disposal problems of the resulting by-products, are not feasible on a commercial scale.

BROAD DESCRIPTION OF THE INVENTION

The object of the invention is to provide a simple process, feasible on a large scale, for the production of gamma-butyrobetaine from butyrolactone, which provides good yields and is quite safe from the ecological aspect.

The object of the invention is achieved by the process according to the invention. The invention process involves the production of gamma-butyrobetaine. The process includes converting gamma-butyrolactone with hydrogen chloride to gamma-chlorobutyric acid. The latter, without isolation, is converted with a lower aliphatic alcohol into the corresponding gamma-chlorobutyric acid lower alkyl ester. The lower alkyl ester is converted with trimethylamine to trimethylammonium butyric acid lower alkyl ester chloride. The latter, without isolation, is finally saponified with a base to the end product.

DETAILED DESCRIPTION OF THE INVENTION

In a first step, gamma-butyrolactone is converted with hydrogen chloride into the gamma-chlorobutyric acid. The operation is suitably performed at a pressure of 1 to 25 bars, preferably at 8 to 20 bars. In this case, the reaction temperature can vary between 40° and 150° C., preferably between 80° and 120° C.

The hydrogen chloride is usually used in an excess of 5 to 40 percent relative to the gamma-butyrolactone. The conversion to gamma-chlorobutyric acid lasts about 2 to 10 hours and generally takes place practically quantitatively. An advantage of the process according to the invention is that the gamma-chlorobutyric acid does not have to be isolated but the reaction solution of the first step can be added directly to the lower aliphatic alcohol necessary for the ester formation. The hydrogen chloride excess from the first step can, thus, function directly as an esterification catalyst. But it can prove necessary to supply additional hydrogen chloride for the esterification.

Methanol, ethanol, propanols and butanols, preferably methanol or ethanol, are suitably used as the lower aliphatic alcohols.

The esterification reaction advantageously takes place at a pressure of 1 to 15 bars, but advantageously at 1 to 10 bars, and at a temperature of suitably 40° to 150° C., preferably 70° to 120° C.

But it is also possible to perform the conversion of gamma-butyrolactone to gamma-chlorobutyric acid ester in one step. For this purpose, the reactants of gamma-butyrolactone, hydrogen chloride and the corresponding alcohol are added together and converted directly to the corresponding gamma-chlorobutyric acid ester at a pressure of 1 to 10 bars and a temperature of 40° to 150° C.

In the third step, the conversion of the gamma-chlorobutyric acid ester with trimethylamine to trimethylammonium butyric acid ester chloride takes place. Suitably this reaction is performed at a pressure of 1 to 10 bars and a temperature of 20° to 180° C., advantageously at 80° to 150° C.

The trimethylamine can be added in a slight excess or in a stoichiometric amount, but preferably in a small excess. It is advantageous to use the alcohol corresponding to the ester radical as the solvent. But trimethylamine-soluble solvents, such as, toluene, can also be used. The conversion of the gamma-trimethylammonium butyric acid ester chloride generally lasts 2 to 6 hours and takes place practically quantitatively.

The reaction solution can further be fed directly to the last step of the saponification.

In principle, all strong bases can be used as bases for the saponification. But preferably aqueous solutions of inorganic bases, such as, alkaline-earth or alkali hydroxides (e.g., NaOH or KOH) or alkaline-earth or alkali carbonates (e.g., sodium carbonate), are used. A reaction temperature of 20° to 100° C. has proved advantageous for the saponification.

Working up or purification of the gamma-butyrobetaine from the reaction solution——adapted to further uses——can take place, e.g., by desalination by ion exchangers, specific crystallization methods or by electrodialysis. The latter method is successfully used to obtain a completely desalted gamma-butyrobetaine solution which optionally, after dilution, can be fed directly to a microbiological carnitine synthesis.

The gamma-butyrobetaine produced according to the process of the invention generally exhibits a purity greater than 99.5 percent. Further, with the new process an overall yield of gamma-butyrobetaine greater than 65 percent, relative to gamma-butyrolactone, is achieved.

U.S. Pat. No. 4,708,936 discloses a process for the continuous production of L-carnitine by the microbiological method. A microorganism of the strain DSM No. 3225 (HK 1331b) type is cultivated in a bioreactor with γ-butyrobetaine in the presence of a growth substrate. The culture fluid passes outside of the bioreactor in a circulation in which a separation of the cell is carried out. A quantity of cell-free solution, which is as large as the amount fed to the bioreactor as a substrate, is withdrawn from the bioreactor. The L-carnitine is separated from the cell-free solution.

EXAMPLE (a) Production of gamma-chlorobutyric acid ethyl ester 51.7 kg (0.6 kmol) of gamma-butyrolactone (100 percent) was placed in an enamel pressure agitator. The closed system was heated to 100° C. with good agitation, and starting from 60° C. a total of about 26.5 kg (0.72 kmol) of HCl was pressed on. The temperature and pressure quickly rose, caused by the exothermia. The addition of HCl and heat output were regulated so that the reaction could be performed isothermally at 100° C. and isobarically at 11 bars of pressure. Addition was continued until no more HCl was absorbed (about 5 to 6 hours). Then it was cooled to 20° C. and the residual HCl was discharged. Then 62.3 kg (1.35 kmol) of ethanol was added to the reaction solution. Then 2 kg (0.055 kmol) of HCl was again pressed on. It was heated to 100° C. and kept at this temperature for 2 hours (pressure was 6 bars) and then cooled to 20° C. The solution was then mixed with 92 kg of toluene and made basic with 23 kg of aqueous NaOH (30 percent) (pH 8 to 8.5). The phases were separated and the organic phase was washed with 26 kg of water. The combined water phases were again extracted with 46 kg of toluene. The organic phase was distilled. Thus, toluene, ethanol and water were separated. 87 kg of crude gamma-chlorobutyric acid ethyl ester (content 88 percent) remained as still residue, which could be used directly in the following step. The yield was 85 percent, relative to the gamma-butyrolactone.

(b) Production of gamma-butyrobetaine 159 kg (0.92 kmol) of crude gamma-chlorobutyric acid ethyl ester (content 88 percent) and 107 kg (2.3 kmol) of ethanol were placed in a pressure agitator. Then 57 kg (0.96 kmol) of trimethylamine was added in 15 to 30 minutes. The temperature in this case rose to 30° to 50° C. Then heating to 130° C. was performed. The pressure in this case rose to 5 to 7 bars and then dropped back to about 4 bars. After a stable pressure was reached, it was cooled to 20° C. and the remaining triethylamine was removed. The reaction solution was adjusted to a pH greater than 11 with 138 kg of aqueous NaOH (30 percent). Then it was kept at 60° C. for 1 hour and the pH was optionally readjusted. Then it was cooled to 20° C. and the precipitated NaCl was filtered off. After removal by distillation of the excess triethylamine and solvent, the residue was diluted with water. This solution was adjusted to pH 8, filtered and desalted by electrodialysis. The resultant solution contained 32 percent of gamma-butyrobetaine corresponding to a yield of 80 percent, relative to the gamma-chlorobutyric acid ethyl ester. The content was 99.5 percent (HPLC determination of a dehydrated specimen).

What is claimed is:

1. Process of the production of gamma-butyrobetaine, comprising (a) conducting a step consisting of converting gamma-butyrolactone only with an excess of 5 to 40 weight percent, relative to the gamma-butyrolactone, of hydrogen chloride at a pressure of 1 to 25 bars and a temperature of 40° to 150° C. to obtain gamma-chlorobutyric acid, (b) a step consisting of converting the gamma-chlorobutyric acid from step (a), without isolation, only with a lower aliphatic alcohol selected from the group consisting of methanol, ethanol, a propanol and a butanol, in the presence of an amount of hydrogen chloride sufficient to act as an esterification catalyst at a pressure of 1 to 15 bars and a temperature of 40° to 150° C. to obtain the corresponding gamma-chlorobutyric acid lower alkyl ester, (c) converting the corresponding gamma-chlorobutyric acid lower alkyl ester with trimethylamine to trimethylammonium butyric acid lower alkyl ester chloride, the conversion being done at a pressure of 1 to 10 bars and a temperature of 20° to 180° C., and (d) saponifying the trimethylammonium butyric acid lower alkyl ester chloride, without isolation, with a base to the gamma-butyrobetaine, the saponficiation being done at a temperature of 20° to 100° C.

2. Process of the production of gamma-butyrobetaine, comprising (a) conducting a step consisting of converting gamma-butyrolactone only with an excess of 5 to 40 weight percent, relative to the gamma-butyrolactone, of hydrogen chloride at a pressure of 1 to 25 bars and a temperature of 40° to 150° C. to obtain gamma-chlorobutyric acid, (b), then without any intermediate step between this step and step (a), discharging the residual hydrogen chloride, (c), then without any intermediate step between this step and step (b), conducting a step consisting of converting the gamma-chlorobutyric acid from step (a), without isolation, only with a lower aliphatic alcohol selected from the group consisting of methanol, ethanol, a propanol and a butanol, in the presence of an amount of hydrogen chloride sufficient to act as an esterification catalyst at a pressure of 1 to 15 bars and a temperature of 40° to 150° C. to obtain the corresponding gamma-chlorobutyric acid lower alkyl ester, (d) converting the corresponding gamma-chlorobutyric acid lower alkyl ester with trimethylamine to trimethylammonium butyric acid lower alkyl ester chloride, the conversion being done at a pressure of 1 to 10 bars and a temperature of 20° to 180° C., and (e) saponifying the trimethylammonium butyric acid lower alkyl ester chloride, without isolation, with a base to the gamma-butyrobetaine, the saponfication being done at a temperature of 20° to 100° C.

3. Process according to claim 1 wherein methanol or ethanol is used as the lower aliphatic alcohol.

4. Process according to claim 2 wherein methanol or ethanol is used as the lower aliphatic alcohol.

* * * * *